US011603400B2

(12) United States Patent
Dykes et al.

(10) Patent No.: US 11,603,400 B2
(45) Date of Patent: *Mar. 14, 2023

(54) METHODS FOR RAISING ANTIBODIES

(71) Applicant: DNAE Group Holdings Limited, London (GB)

(72) Inventors: Colin Dykes, Albuquerque, NM (US); Sergey A. Dryga, Albuquerque, NM (US); Lisa-Jo Ann Clarizia, Albuquerque, NM (US); Eddie W. Adams, Albuquerque, NM (US); Meghan E. Norvell, Albuquerque, NM (US)

(73) Assignee: DNAE Group Holdings Limited, London (GB)

( * ) Notice: Subject to any disclaimer, the term of this patent is extended or adjusted under 35 U.S.C. 154(b) by 1184 days.

This patent is subject to a terminal disclaimer.

(21) Appl. No.: 16/011,158

(22) Filed: Jun. 18, 2018

(65) Prior Publication Data

US 2019/0153075 A1  May 23, 2019

Related U.S. Application Data

(63) Continuation of application No. 14/132,099, filed on Dec. 18, 2013, now Pat. No. 10,000,557.

(60) Provisional application No. 61/739,511, filed on Dec. 19, 2012.

(51) Int. Cl.
| | |
|---|---|
| *C12Q 1/68* | (2018.01) |
| *C40B 50/06* | (2006.01) |
| *G16B 20/20* | (2019.01) |
| *G16B 20/40* | (2019.01) |
| *C07K 16/12* | (2006.01) |
| *G16B 10/00* | (2019.01) |

(52) U.S. Cl.
CPC ............... *C07K 16/12* (2013.01); *C12Q 1/68* (2013.01); *C40B 50/06* (2013.01); *G16B 10/00* (2019.02); *G16B 20/20* (2019.02); *G16B 20/40* (2019.02)

(58) Field of Classification Search
CPC .. A61K 2039/507; C07K 16/00; C07K 16/12; C12Q 1/68; C40B 40/10; C40B 50/06; G01N 33/68; G16B 20/20; G16B 20/40
See application file for complete search history.

(56) References Cited

U.S. PATENT DOCUMENTS

| | | |
|---|---|---|
| 3,970,518 A | 7/1976 | Giaever |
| 4,018,886 A | 4/1977 | Giaever |
| 4,180,563 A | 12/1979 | Fauve |
| 4,230,685 A | 10/1980 | Senyei et al. |
| 4,267,234 A | 5/1981 | Rembaum |
| 4,434,237 A | 2/1984 | Dinarello |
| 4,452,773 A | 6/1984 | Molday |
| 4,551,435 A | 11/1985 | Liberti et al. |
| 4,554,088 A | 11/1985 | Whitehead et al. |
| 4,659,678 A | 4/1987 | Forrest et al. |
| 4,677,055 A | 6/1987 | Dodin et al. |
| 4,683,195 A | 7/1987 | Mullis et al. |
| 4,683,202 A | 7/1987 | Mullis |
| 4,695,393 A | 9/1987 | Chagnon et al. |
| 4,795,698 A | 1/1989 | Owen et al. |
| 4,851,330 A | 7/1989 | Kohne |
| 4,901,018 A | 2/1990 | Lew |
| 4,925,788 A | 5/1990 | Liberti |
| 4,942,124 A | 7/1990 | Church |
| 4,988,617 A | 1/1991 | Landegren et al. |
| 5,004,699 A | 4/1991 | Winters |
| 5,047,321 A | 9/1991 | Loken et al. |
| 5,057,413 A | 10/1991 | Terstappen et al. |
| 5,089,386 A | 2/1992 | Stackebrandt et al. |
| 5,108,933 A | 4/1992 | Liberti et al. |
| 5,136,095 A | 8/1992 | Tarnowski et al. |
| 5,149,625 A | 9/1992 | Church et al. |
| 5,164,297 A | 11/1992 | Josephson et al. |
| 5,186,827 A | 2/1993 | Liberti et al. |
| 5,200,084 A | 4/1993 | Liberti et al. |
| 5,229,724 A | 7/1993 | Zeiger |
| 5,234,816 A | 8/1993 | Terstappen |
| 5,242,794 A | 9/1993 | Whiteley et al. |
| 5,254,460 A | 10/1993 | Josephson et al. |
| 5,270,163 A | 12/1993 | Gold et al. |
| 5,338,687 A | 8/1994 | Lee et al. |
| 5,342,790 A | 8/1994 | Levine et al. |
| 5,460,979 A | 10/1995 | Levine et al. |
| 5,466,574 A | 11/1995 | Liberti et al. |
| 5,494,810 A | 2/1996 | Barany et al. |
| 5,512,332 A | 4/1996 | Liberti et al. |
| 5,541,072 A | 7/1996 | Wang et al. |
| 5,583,024 A | 12/1996 | McElroy et al. |
| 5,583,033 A | 12/1996 | Terstappen et al. |
| 5,597,531 A | 1/1997 | Liberti et al. |
| 5,604,097 A | 2/1997 | Brenner |
| 5,605,805 A | 2/1997 | Verwer et al. |
| 5,622,831 A | 4/1997 | Liberti et al. |
| 5,622,853 A | 4/1997 | Terstappen et al. |

(Continued)

FOREIGN PATENT DOCUMENTS

| | | |
|---|---|---|
| CA | 2 342 047 A1 | 9/2001 |
| EP | 1 304 581 A2 | 4/2003 |

(Continued)

OTHER PUBLICATIONS

Latreille et al. Optical mapping as a routine tool for bacterial genome sequence finishing. BMC Genomics. Sep. 14, 2007, vol. 8, pp. 321-326. (Year: 2007).*

(Continued)

*Primary Examiner* — Jeffrey E. Russel
(74) *Attorney, Agent, or Firm* — Brown Rudnick LLP

(57) ABSTRACT

The present invention generally relates to methods of generating antibodies against a species of pathogen that involve identifying the pathogen that is most genetically representative of member of pathogen species and using the identified pathogen to generate an antibody.

13 Claims, No Drawings

(56) References Cited

U.S. PATENT DOCUMENTS

| | | |
|---|---|---|
| 5,636,400 A | 6/1997 | Young |
| 5,646,001 A | 7/1997 | Terstappen et al. |
| 5,654,636 A | 8/1997 | Sweedler et al. |
| 5,660,990 A | 8/1997 | Rao et al. |
| 5,674,713 A | 10/1997 | McElroy et al. |
| 5,677,133 A | 10/1997 | Oberhardt |
| 5,681,478 A | 10/1997 | Lea et al. |
| 5,684,401 A | 11/1997 | Peck et al. |
| 5,695,934 A | 12/1997 | Brenner |
| 5,695,946 A | 12/1997 | Benjamin et al. |
| 5,698,271 A | 12/1997 | Liberti et al. |
| 5,700,673 A | 12/1997 | McElroy et al. |
| 5,741,714 A | 4/1998 | Liberti |
| 5,768,089 A | 6/1998 | Finnigan |
| 5,770,461 A | 6/1998 | Sakazume et al. |
| 5,773,307 A | 6/1998 | Colin et al. |
| 5,776,710 A | 7/1998 | Levine et al. |
| 5,795,470 A | 8/1998 | Wang et al. |
| 5,821,066 A | 10/1998 | Pyle et al. |
| 5,834,217 A | 11/1998 | Levine et al. |
| 5,840,580 A | 11/1998 | Terstappen et al. |
| 5,846,719 A | 12/1998 | Brenner et al. |
| 5,863,722 A | 1/1999 | Brenner |
| 5,866,099 A | 2/1999 | Owen et al. |
| 5,869,252 A | 2/1999 | Bouma et al. |
| 5,876,593 A | 3/1999 | Liberti et al. |
| 5,925,573 A | 7/1999 | Colin et al. |
| 5,935,825 A | 8/1999 | Nishimura et al. |
| 5,948,412 A | 9/1999 | Murphy |
| 5,955,583 A | 9/1999 | Beavo et al. |
| 5,985,153 A | 11/1999 | Dolan et al. |
| 5,993,665 A | 11/1999 | Terstappen et al. |
| 6,013,188 A | 1/2000 | Terstappen et al. |
| 6,013,532 A | 1/2000 | Liberti et al. |
| 6,046,585 A | 4/2000 | Simmonds |
| 6,060,882 A | 5/2000 | Doty |
| 6,097,188 A | 8/2000 | Sweedler et al. |
| 6,100,099 A | 8/2000 | Gordon et al. |
| 6,120,856 A | 9/2000 | Liberti et al. |
| 6,136,182 A | 10/2000 | Dolan et al. |
| 6,136,554 A * | 10/2000 | Bochner ............... C12N 1/20 435/243 |
| 6,138,077 A | 10/2000 | Brenner |
| 6,146,838 A | 11/2000 | Williams et al. |
| 6,150,516 A | 11/2000 | Brenner et al. |
| 6,172,214 B1 | 1/2001 | Brenner |
| 6,172,218 B1 | 1/2001 | Brenner |
| 6,194,900 B1 | 2/2001 | Freeman et al. |
| 6,228,624 B1 | 5/2001 | Terstappen |
| 6,235,475 B1 | 5/2001 | Brenner et al. |
| 6,236,205 B1 | 5/2001 | Ludeke et al. |
| 6,242,915 B1 | 6/2001 | Hurd |
| 6,265,150 B1 | 7/2001 | Terstappen et al. |
| 6,287,791 B1 | 9/2001 | Terstappen et al. |
| 6,307,372 B1 | 10/2001 | Sugarman et al. |
| 6,326,787 B1 | 12/2001 | Cowgill |
| 6,348,318 B1 | 2/2002 | Valkirs |
| 6,352,828 B1 | 3/2002 | Brenner |
| 6,361,749 B1 | 3/2002 | Terstappen et al. |
| 6,361,944 B1 | 3/2002 | Mirkin et al. |
| 6,365,362 B1 | 4/2002 | Terstappen et al. |
| 6,395,879 B1 | 5/2002 | Mandrell et al. |
| 6,397,094 B1 | 5/2002 | Ludeke et al. |
| 6,404,193 B1 | 6/2002 | Dourdeville |
| 6,456,072 B1 | 9/2002 | Webb et al. |
| 6,469,636 B1 | 10/2002 | Baird et al. |
| 6,487,437 B1 | 11/2002 | Viswanathan et al. |
| 6,495,357 B1 | 12/2002 | Fuglsang et al. |
| 6,512,941 B1 | 1/2003 | Weiss et al. |
| 6,514,415 B2 | 2/2003 | Hatch et al. |
| 6,551,843 B1 | 4/2003 | Rao et al. |
| 6,555,324 B1 | 4/2003 | Olweus et al. |
| 6,582,938 B1 | 6/2003 | Su et al. |
| 6,587,706 B1 | 7/2003 | Viswanathan |
| 6,594,517 B1 | 7/2003 | Nevo |
| 6,620,627 B1 | 9/2003 | Liberti et al. |
| 6,623,982 B1 | 9/2003 | Liberti et al. |
| 6,623,983 B1 | 9/2003 | Terstappen et al. |
| 6,645,731 B2 | 11/2003 | Terstappen et al. |
| 6,660,159 B1 | 12/2003 | Terstappen et al. |
| 6,696,838 B2 | 2/2004 | Raftery et al. |
| 6,700,379 B2 | 3/2004 | Peck et al. |
| 6,788,061 B1 | 9/2004 | Sweedler et al. |
| 6,790,366 B2 | 9/2004 | Terstappen et al. |
| 6,818,395 B1 | 11/2004 | Quake et al. |
| 6,822,454 B2 | 11/2004 | Peck et al. |
| 6,845,262 B2 | 1/2005 | Albert et al. |
| 6,858,384 B2 | 2/2005 | Terstappen et al. |
| 6,867,021 B2 | 3/2005 | Maes et al. |
| 6,876,200 B2 | 4/2005 | Anderson et al. |
| 6,890,426 B2 | 5/2005 | Terstappen et al. |
| 6,898,430 B1 | 5/2005 | Liberti et al. |
| 6,913,889 B2 * | 7/2005 | Gerbi ............... A61P 33/02 435/6.13 |
| 6,914,538 B2 | 7/2005 | Baird et al. |
| 6,958,609 B2 | 10/2005 | Raftery et al. |
| 7,011,794 B2 | 3/2006 | Kagan et al. |
| 7,056,657 B2 | 6/2006 | Terstappen et al. |
| 7,078,224 B1 | 7/2006 | Bitner et al. |
| 7,096,057 B2 | 8/2006 | Hockett et al. |
| 7,141,978 B2 | 11/2006 | Peck et al. |
| 7,169,560 B2 | 1/2007 | Lapidus et al. |
| 7,200,430 B2 | 4/2007 | Thomas et al. |
| 7,202,667 B2 | 4/2007 | Barbie |
| RE39,793 E | 8/2007 | Brenner |
| 7,271,592 B1 | 9/2007 | Gerald, II et al. |
| 7,274,191 B2 | 9/2007 | Park et al. |
| 7,282,180 B2 | 10/2007 | Tibbe et al. |
| 7,282,337 B1 | 10/2007 | Harris |
| 7,282,350 B2 | 10/2007 | Rao et al. |
| 7,304,478 B2 | 12/2007 | Tsuda et al. |
| 7,332,288 B2 | 2/2008 | Terstappen et al. |
| 7,345,479 B2 | 3/2008 | Park et al. |
| 7,393,665 B2 | 7/2008 | Brenner |
| 7,403,008 B2 | 7/2008 | Blank et al. |
| 7,405,567 B2 | 7/2008 | McDowell |
| 7,523,385 B2 | 4/2009 | Nguyen et al. |
| 7,537,897 B2 | 5/2009 | Brenner et al. |
| 7,544,473 B2 | 6/2009 | Brenner |
| 7,564,245 B2 | 7/2009 | Lee |
| 7,666,308 B2 | 2/2010 | Scholtens et al. |
| 7,688,777 B2 | 3/2010 | Liberti, Jr. et al. |
| 7,764,821 B2 | 7/2010 | Coumans et al. |
| 7,815,863 B2 | 10/2010 | Kagan et al. |
| 7,828,968 B2 | 11/2010 | Tibbe et al. |
| 7,863,012 B2 | 1/2011 | Rao et al. |
| 7,901,950 B2 | 3/2011 | Connelly et al. |
| 7,943,397 B2 | 5/2011 | Tibbe et al. |
| 8,067,938 B2 | 11/2011 | McDowell |
| 8,102,176 B2 | 1/2012 | Lee |
| 8,110,101 B2 | 2/2012 | Tibbe et al. |
| 8,111,669 B2 | 2/2012 | Liberti, Jr. et al. |
| 8,128,890 B2 | 3/2012 | Droog et al. |
| 8,841,104 B2 | 9/2014 | Dryga et al. |
| 8,889,368 B2 | 11/2014 | Barbreau et al. |
| 9,389,225 B2 | 7/2016 | Dryga et al. |
| 9,428,547 B2 | 8/2016 | Dryga et al. |
| 9,434,940 B2 | 9/2016 | Dykes |
| 9,476,812 B2 | 10/2016 | Dryga et al. |
| 9,551,704 B2 | 1/2017 | Norvell |
| 9,562,896 B2 | 2/2017 | Esch et al. |
| 9,599,610 B2 | 3/2017 | Sitdikov et al. |
| 9,671,395 B2 | 6/2017 | Dryga et al. |
| 9,696,302 B2 | 7/2017 | Dryga et al. |
| 9,869,671 B2 | 1/2018 | Dryga et al. |
| 9,970,931 B2 | 5/2018 | Dryga et al. |
| 2001/0018192 A1 | 8/2001 | Terstappen et al. |
| 2002/0009759 A1 | 1/2002 | Terstappen et al. |
| 2002/0012669 A1 | 1/2002 | Presnell et al. |
| 2002/0042125 A1 | 4/2002 | Petersen et al. |
| 2002/0098531 A1 | 7/2002 | Fhacker |
| 2002/0130661 A1 | 9/2002 | Raftery et al. |
| 2002/0132228 A1 | 9/2002 | Terstappen et al. |
| 2002/0141913 A1 | 10/2002 | Terstappen et al. |

(56) References Cited

U.S. PATENT DOCUMENTS

| | | |
|---|---|---|
| 2002/0164629 A1 | 11/2002 | Quake et al. |
| 2002/0164659 A1 | 11/2002 | Rao et al. |
| 2002/0172987 A1 | 11/2002 | Terstappen et al. |
| 2003/0003441 A1 | 1/2003 | Colston et al. |
| 2003/0022231 A1 | 1/2003 | Wangh et al. |
| 2003/0054376 A1 | 3/2003 | Mullis et al. |
| 2003/0088181 A1 | 5/2003 | Gleich |
| 2003/0092029 A1 | 5/2003 | Josephson et al. |
| 2003/0129676 A1 | 7/2003 | Terstappen et al. |
| 2003/0144479 A1 * | 7/2003 | Greene ............ C07K 14/70539 530/387.2 |
| 2003/0170613 A1 | 9/2003 | Straus |
| 2003/0186412 A1 * | 10/2003 | Kizaki ................. C12N 9/0008 435/320.1 |
| 2003/0203507 A1 | 10/2003 | Liberti et al. |
| 2003/0206577 A1 | 11/2003 | Liberti et al. |
| 2003/0222648 A1 | 12/2003 | Fan |
| 2004/0004043 A1 | 1/2004 | Terstappen et al. |
| 2004/0018611 A1 | 1/2004 | Ward et al. |
| 2004/0072269 A1 | 4/2004 | Rao et al. |
| 2004/0076990 A1 | 4/2004 | Picard et al. |
| 2004/0087032 A1 | 5/2004 | Chandler et al. |
| 2004/0101443 A1 | 5/2004 | Kagan et al. |
| 2004/0118757 A1 | 6/2004 | Terstappen et al. |
| 2004/0151629 A1 | 8/2004 | Pease et al. |
| 2005/0003464 A1 | 1/2005 | Tibbe et al. |
| 2005/0006990 A1 | 1/2005 | Williquette et al. |
| 2005/0026144 A1 | 2/2005 | Maes et al. |
| 2005/0043521 A1 | 2/2005 | Terstappen et al. |
| 2005/0069900 A1 | 3/2005 | Lentrichia |
| 2005/0079520 A1 | 4/2005 | Wu |
| 2005/0111414 A1 | 5/2005 | Liberti et al. |
| 2005/0128985 A1 | 6/2005 | Liberti et al. |
| 2005/0181353 A1 | 8/2005 | Rao et al. |
| 2005/0181463 A1 | 8/2005 | Rao et al. |
| 2005/0245814 A1 | 11/2005 | Anderson et al. |
| 2006/0002804 A1 | 1/2006 | Jiang et al. |
| 2006/0024756 A1 | 2/2006 | Tibbe et al. |
| 2006/0115380 A1 | 6/2006 | Kagan et al. |
| 2006/0129237 A1 | 6/2006 | Imran |
| 2006/0129327 A1 | 6/2006 | Kim et al. |
| 2006/0147901 A1 | 7/2006 | Jan et al. |
| 2006/0194192 A1 | 8/2006 | Rao et al. |
| 2006/0233712 A1 | 10/2006 | Penades et al. |
| 2006/0257847 A1 | 11/2006 | Scholtens et al. |
| 2006/0257945 A1 | 11/2006 | Masters et al. |
| 2006/0281094 A1 | 12/2006 | Squirrel et al. |
| 2006/0292555 A1 | 12/2006 | Xu et al. |
| 2007/0031850 A1 * | 2/2007 | Mounts ................ C12Q 1/6837 435/6.15 |
| 2007/0037173 A1 | 2/2007 | Allard et al. |
| 2007/0037231 A1 | 2/2007 | Sauer-Budge et al. |
| 2007/0090836 A1 | 4/2007 | Xiang et al. |
| 2007/0114181 A1 | 5/2007 | Li et al. |
| 2007/0116602 A1 | 5/2007 | Lee |
| 2007/0117158 A1 | 5/2007 | Coumans et al. |
| 2007/0152669 A1 | 7/2007 | Park et al. |
| 2007/0152670 A1 | 7/2007 | Park et al. |
| 2007/0154960 A1 | 7/2007 | Connelly et al. |
| 2007/0166835 A1 | 7/2007 | Bobrow et al. |
| 2007/0183935 A1 | 8/2007 | Clemmens et al. |
| 2007/0231926 A1 | 10/2007 | Ikeda |
| 2007/0264629 A1 | 11/2007 | Holmes et al. |
| 2007/0296413 A1 | 12/2007 | Park et al. |
| 2008/0026451 A1 | 1/2008 | Braman et al. |
| 2008/0042650 A1 | 2/2008 | McDowell |
| 2008/0081330 A1 | 4/2008 | Kahvejian |
| 2008/0099715 A1 | 5/2008 | Adams et al. |
| 2008/0113350 A1 | 5/2008 | Terstappen |
| 2008/0135490 A1 | 6/2008 | Li et al. |
| 2008/0199851 A1 | 8/2008 | Egan et al. |
| 2008/0204011 A1 | 8/2008 | Shoji |
| 2008/0204022 A1 | 8/2008 | Sillerud et al. |
| 2008/0272788 A1 | 11/2008 | McDowell |
| 2008/0286838 A1 | 11/2008 | Yuan et al. |
| 2008/0315875 A1 | 12/2008 | Sillerud |
| 2009/0026082 A1 | 1/2009 | Rothberg et al. |
| 2009/0053799 A1 | 2/2009 | Chang-Yen et al. |
| 2009/0061456 A1 | 3/2009 | Allard et al. |
| 2009/0061476 A1 | 3/2009 | Tibbe et al. |
| 2009/0061477 A1 | 3/2009 | Tibbe et al. |
| 2009/0127589 A1 | 5/2009 | Rothberg et al. |
| 2009/0134869 A1 | 5/2009 | Lee |
| 2009/0136946 A1 | 5/2009 | Connelly et al. |
| 2009/0146658 A1 | 6/2009 | McDowell et al. |
| 2009/0148847 A1 | 6/2009 | Kokoris et al. |
| 2009/0156572 A1 | 6/2009 | Ikeura et al. |
| 2009/0173681 A1 | 7/2009 | Siddiqi |
| 2009/0191535 A1 | 7/2009 | Connelly et al. |
| 2009/0227044 A1 | 9/2009 | Dosev et al. |
| 2009/0246796 A1 | 10/2009 | Bernard et al. |
| 2009/0256572 A1 | 10/2009 | McDowell |
| 2009/0258365 A1 | 10/2009 | Terstappen et al. |
| 2009/0286264 A1 | 11/2009 | Scholtens et al. |
| 2010/0035252 A1 | 2/2010 | Rothberg et al. |
| 2010/0061890 A1 | 3/2010 | Miller et al. |
| 2010/0068723 A1 | 3/2010 | Jovanovich et al. |
| 2010/0072994 A1 | 3/2010 | Lee et al. |
| 2010/0129785 A1 | 5/2010 | Pris et al. |
| 2010/0137143 A1 | 6/2010 | Rothberg et al. |
| 2010/0144005 A1 | 6/2010 | Bin Kingombe et al. |
| 2010/0184033 A1 | 7/2010 | West et al. |
| 2010/0188073 A1 | 7/2010 | Rothberg et al. |
| 2010/0197507 A1 | 8/2010 | Rothberg et al. |
| 2010/0219824 A1 | 9/2010 | Sillerud et al. |
| 2010/0225315 A1 | 9/2010 | McDowell |
| 2010/0282617 A1 | 11/2010 | Rothberg et al. |
| 2010/0282788 A1 | 11/2010 | Liberti |
| 2010/0291666 A1 | 11/2010 | Collier et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2010/0316651 A1 * | 12/2010 | Scannon ................... A61P 9/10 424/158.1 |
| 2010/0326587 A1 | 12/2010 | Kagan et al. |
| 2011/0014686 A1 | 1/2011 | Tibbe et al. |
| 2011/0018538 A1 | 1/2011 | Lee |
| 2011/0044527 A1 | 2/2011 | Tibbe et al. |
| 2011/0046475 A1 | 2/2011 | Assif et al. |
| 2011/0052037 A1 | 3/2011 | Coumans et al. |
| 2011/0059444 A1 | 3/2011 | Stromberg et al. |
| 2011/0070586 A1 | 3/2011 | Slezak et al. |
| 2011/0086338 A1 | 4/2011 | Hwang et al. |
| 2011/0091987 A1 | 4/2011 | Weissleder et al. |
| 2011/0098623 A1 | 4/2011 | Zhang et al. |
| 2011/0104718 A1 | 5/2011 | Rao et al. |
| 2011/0137018 A1 | 6/2011 | Chang-Yen et al. |
| 2011/0183398 A1 | 7/2011 | Dasaratha et al. |
| 2011/0262893 A1 | 10/2011 | Dryga et al. |
| 2011/0262925 A1 | 10/2011 | Dryga et al. |
| 2011/0262926 A1 | 10/2011 | Esch et al. |
| 2011/0262927 A1 | 10/2011 | Dryga et al. |
| 2011/0262932 A1 | 10/2011 | Esch et al. |
| 2011/0262933 A1 | 10/2011 | Dryga et al. |
| 2011/0262989 A1 | 10/2011 | Clarizia et al. |
| 2011/0263833 A1 | 10/2011 | Dryga et al. |
| 2011/0300551 A1 | 12/2011 | Rao et al. |
| 2011/0300609 A1 | 12/2011 | Lim et al. |
| 2011/0301042 A1 | 12/2011 | Steinmann et al. |
| 2012/0045828 A1 | 2/2012 | Davis et al. |
| 2012/0094275 A1 | 4/2012 | Rao et al. |
| 2012/0100546 A1 | 4/2012 | Lowery, Jr. et al. |
| 2012/0112744 A1 | 5/2012 | McDowell et al. |
| 2013/0109590 A1 | 5/2013 | Clarizia et al. |
| 2013/0196341 A1 | 8/2013 | Neely et al. |
| 2013/0203634 A1 | 8/2013 | Jovanovich et al. |
| 2013/0316355 A1 | 11/2013 | Dryga et al. |
| 2014/0100136 A1 | 4/2014 | Clarizia et al. |
| 2014/0170021 A1 | 6/2014 | Dryga |
| 2014/0170639 A1 | 6/2014 | Norvell |
| 2014/0170640 A1 | 6/2014 | Dykes |
| 2014/0170641 A1 | 6/2014 | Macemon |
| 2014/0170652 A1 | 6/2014 | Sitdikov et al. |

(56) References Cited

U.S. PATENT DOCUMENTS

| | | |
|---|---|---|
| 2014/0170667 A1 | 6/2014 | Dykes et al. |
| 2014/0170669 A1 | 6/2014 | Vandervest |
| 2014/0170727 A1 | 6/2014 | Dryga et al. |
| 2014/0171340 A1 | 6/2014 | Dykes et al. |
| 2015/0212079 A1 | 7/2015 | Dryga et al. |

FOREIGN PATENT DOCUMENTS

| | | |
|---|---|---|
| EP | 2138835 A1 | 12/2009 |
| EP | 2261650 A2 | 12/2010 |
| WO | 1988/003957 A1 | 6/1988 |
| WO | 89/06699 A1 | 7/1989 |
| WO | 90/08841 A1 | 8/1990 |
| WO | 91/02811 A1 | 3/1991 |
| WO | 92/08805 A1 | 5/1992 |
| WO | 92/15883 A1 | 9/1992 |
| WO | 9217609 A1 | 10/1992 |
| WO | 95/31481 A1 | 11/1995 |
| WO | 98/20148 A1 | 5/1998 |
| WO | 99/53320 A1 | 10/1999 |
| WO | 31/73460 A1 | 10/2001 |
| WO | 32/98364 A2 | 12/2002 |
| WO | 2005/026762 A1 | 3/2005 |
| WO | 2005106480 A1 | 11/2005 |
| WO | 2007/018601 A1 | 2/2007 |
| WO | 2007/123345 A1 | 11/2007 |
| WO | 2007/135099 A1 | 11/2007 |
| WO | 2007123342 A1 | 11/2007 |
| WO | 2008/119054 A1 | 10/2008 |
| WO | 2008/139419 A1 | 11/2008 |
| WO | 2008147530 A1 | 12/2008 |
| WO | 2009/048673 A2 | 4/2009 |
| WO | 2009/055587 A1 | 4/2009 |
| WO | 2009072003 A2 | 6/2009 |
| WO | 2009/122216 A1 | 10/2009 |
| WO | 2010036827 A1 | 4/2010 |
| WO | 2011/019874 A1 | 2/2011 |
| WO | 2011/133630 A1 | 10/2011 |
| WO | 2011/133632 A1 | 10/2011 |
| WO | 2011/133759 A1 | 10/2011 |
| WO | 2011/133760 A1 | 10/2011 |

OTHER PUBLICATIONS

Behnia and Webb, Limited-Sample NMR Using Solenoidal Microcoils, Perfluorocarbon Plugs, and Capillary Spinning, Anal. Chem., 70:5326-5331 (1998).

Braslaysky et al., PNAS, 100:3690-3694 (2003).

Brown et al., Methods Enzymol., 68:109 (1979).

Bruno et al., "Development of an Immunomagnetic Assay System for Rapid Detection of Bacteria and Leukocytes in Body Fluids," J Mol Recog, 9 (1996) 474-479.

Burtis et al. (Burtis, C.A. (Ed.), Tietz Textbook of Clinical Chemistry, 3rd Edition (1999), W.B. Saunders Company, Philadelphia, PA, pp. 1793-1794).

Butter et al., 2002, Synthesis and properties of iron ferrofluids, J. Magn. Magn. Mater. 252:1-3.

Byrne, et al., Antibody-Based Sensors: Principles, Problems and Potential for Detection of Pathogens and Associated Toxins, Sensors, 9:4407-4445 (2009).

Campuzano, et al., Bacterial Isolation by Lectin Modified Microengines, Nano Lett. Jan. 11, 2012; 12(1): 396-401.

Cann et al., Proc. Natl. Acad. Sci. 95:14250 (1998).

Cariello et al., Nucl Acids Res, 19:4193 (1991).

Carroll, N. M., E. E. Jaeger, et al. (2000). "Detection of and discrimination between grampositive and gram-negative bacteria in intraocular samples by using nested PCR." J Clin 15 Microbiol 38(5): 1753-1757.

Chandler et al., Automated immunomagnetic separation and microarray detection of E. Coli O157:H7 from poultry carcass rinse, Int. J. Food Micro., 70 (2001) 143-154.

Chapman, et al., Use of commercial enzyme immunoassays and immunomagnetic separation systems for detecting *Escherichia coli* O157 in bovine fecal samples, Applied and Environmental Microbiology, 63(7):2549-2553 (1997).

Cheng et al, 2012, Concentration and detection of bacteria in virtual environmental samples based on non-immunomagnetic separation and quantum dots by using a laboratory-made system, Proc. of SPIE:82310Y-1-82310Y-18.

Chien et al., J. Bacteriol, 127:1550 (1976).

Chungang Wang et al. "Multifunctional Magnetic-OPtical Nanoparticle Probes for Simultaneous Detection, Separation, and Thermal Ablation of Multiple Pathogens", Small, vol. 6, No. 2 Jan. 18, 2010, pp. 283-289.

Ciobanu and Pennington, 3D Micron-scale MRI of Single Biological Cells, Solid State Nucl. Magn. Reson., 25:138-141 (2004).

Cold Spring Harbor Protocols, Recipe for Dulbecco's phosphate-buffered saline (Dulbecco's PBS, 2009, retrieved from http://cshprotocols.cshlp.Org/content/2009/3/pdb.rec11725.full?text_only=true on Mar. 9, 2015, one page.

Cooper et al., 2011, A micromagnetic flux concentrator device for isolation and visualization of pathogens. 15th International Conference on Miniaturized Systems for Chemistry and Life Sciences. Oct. 2-6, 2011, Seattle, Washington, USA.

Cross, et al., Choice of Bacteria in Animal Models of Sepsis, Infec. Immun. 61(7):2741-2747 (1983).

Dam et al. "Garlic (*Allium sativum*) Lectins Bind to High Mannose Oligosaccharide Chains", Journal of Biological Chemistry vol. 273, No. 10, Issue of Mar. 6, pp. 5528-5535, 1998.

Diaz et al., Braz J. Med. Res., 31:1239 (1998).

Djukovic, et al., Signal Enhancement in HPLC/Microcoil NMR Using Automated Column Trapping, Anal. Chem., 78:7154-7160 (2006).

DNA Replication 2nd edition, Kornberg and Baker, W.H. Freeman, New York, NY (1991).

Dover, Jason E., et al. "Recent advances in peptide probe-based biosensors for detection of infectious agents." Journal of microbiological methods 78.1 (2009): 10-19.

Drancourt, et al., Diagnosis of Mediterranean Spotted Fever by Indirect Immunofluorescence of Rickettsia conorii in Circulating Endothelial Cells Isolated with Monoclonal Antibody-Coated Immunomagnetic Beads, J. Infectious Diseases, 166(3):660-663, 1992.

Dynabeads® for Immunoassay IVD, retrieved from http://www.invitrogen.com/site/i3s/en/home/Products-and-Services/Applications/DiagnosticsClinical-Research/Bead-based-IVD-Assavs/Bead-based-Immunoassav-iVD.html on May 29, 2013, four pages).

Elnifro, Elfath M., et al. "Multiplex PCR: optimization and application in diagnostic virology." Clinical Microbiology Reviews 13.4 (2000): 559-570.

Engvall, Enzyme immunoassay ELISA and EMIT, Meth. in Enzymol., 70:419-439 (1980).

Extended European Search Report issued in EP 11864030.9, dated Aug. 20, 2014.

Extended European Search Report, dated Oct. 15, 2013 for EP application No. 11772606.7.

Fan, et al., Self-assembly of ordered, robust, three-dimensional gold nanocrystal/silica arrays, Science, 304:567 (2004).

Fenwick et al., 1986, Mechanisms Involved in Protection Provided by Immunization against Core Lipopolysaccarides of *Escherichia coli* J5 from Lethal Haemophilus pleuropneumoniae Infections in Swine, Infection and Immunity 53(2):298-304.

Fu, et al., Rapid Detection of *Escherichia coli* O157:H7 by Immunogmagnetic Separation and Real-time PCR, Int. J. Food Microbiology, 99(1):47-57, (2005).

Fung, M-C., et al. PCR amplification of mRNA directly from a crude cell lysate prepared by thermophilic protease digestion, Nucleic Acids Research, vol. 19 (15), p. 4300, 1991.

Goding, J.W., Conjugation of antibodies with fluorochromes: modifications to the standard methods, J. Immunol. Meth., 13:215 (1976).

Goloshevsky, et al., Development of Low Field Nuclear Magnetic Resonance Microcoils, Rev. Sci. Inst.., 76:024101-1 to 024101-6 (2005).

(56) References Cited

OTHER PUBLICATIONS

Goloshevsky, et al., Integration of Biaxial Planar Gradient Coils and an RF Microcoil for NMR Flow Imaging, Meas. Sci. Technol., 16:505-512 (2005).
Grant, et al., Analysis of Multilayer Radio Frequency Microcoils for Nuclear Magnetic Resonance Spectroscopy, IEEE Trans. Magn., 37:2989-2998 (2001).
Grant, et al., Nmr Spectroscopy of Single Neurons, Magn. Reson. Med., 44:19-22 (2000).
Griffiths et al., 1994, Isolation of high affinity human antibodies directly from large synthetic repertoires. EMBO J. 13(14):3245-3260.
Gu et al., 2003, Using Biofunctional Magentic Nanoparticles to Capture Vancomycin-Resistant Enterococci and Other Gram-Positive Bacteria at Ultralow Concentration, J. Am. Chem. Soc., 125:15702-15703.
Gu et al., 2006, Biofunctional magnetic nanoparticles for protein separation and pathogen detection, Chem. Commun.:941-949.
Halbach, Design of Permanent Multipole Magnets with Oriented Rare Earth Cobalt Material, Nuclear Instrum Methods, 169:1-10 (1980).
Harada, et al., Monoclonal antibody G6K12 specific for membrane-associated differentiation marker of human stratified squamous epithelia and squamous cell carcinoma, J. Oral. Pathol. Med., 22(4):1145-152 (1993).
Harkins and Harrigan, "Labeling of Bacterial Pathogens for Flow Cytometric Detection and Enumeration" Curr Prot Cytom (2004) 11.17.1-11.17.20.
Harris et al., Science 320:106-109 (2008).
Heijnen et al., 2009, Method for rapid detection of viable *Escherichia coli* in water using real-time NASBA, Water Research, 43:3124-3132.
Hijmans, et al., An immunofluorescence procedure for the detection of intracellular immunoglobulins, Clin. Exp. Immunol., 4:457 (1969).
Hinnisdales et al., Biotechniques Res., 19:4193 (1996).
Hirsch, et al., Easily reversible desthiobiotin binding to streptavidin, avidin, and other biotin-binding proteins: uses for protein labeling, detection, and isolation, Anal. Biochem., 208(2):343-57 (2002).
Hoult and Richards, The Signal-to-Noise Ratio of the Nuclear Magnetic Resonance Experiment, J. Magn. Reson., 24:71-85 (1976).
Inai, et al., Immunohistochemical detection of an enamel protein-related epitope in rat bone at an early stage of osteogenesis, Histochemistry, 99(5):335-362 (1993).
International Search Report in PCT/US2013/076649 dated Dec. 19, 2013, 2 pages.
International Search Report in PCT/US2011/33184, dated Jul. 25, 2011, 2 pages.
International Search Report in PCT/US2011/33186, dated Jun. 22, 2011, 1 page.
International Search Report in PCT/US2011/33410, dated Jul. 19, 2011, 2 pages.
International Search Report in PCT/US2011/33411, dated Jun. 22, 2011, 1 page.
International Search Report issued in PCT/US2013/076649, dated Feb. 27, 2014.
IPRP in PCT/US2008/058518, mailed Jul. 7, 2008, 21 pages.
ISR and Written Opinion in PCT/US2008/062473, dated Oct. 29, 2008, 20 pages.
ISR and Written Opinion in PCT/US2008/080983, dated Mar. 3, 2009, 14 pages.
ISR and Written Opinion in PCT/US2009/067577, dated Feb. 5, 2010, 13 pages.
ISR and Written Opinion in PCT/US2011/48447, dated Dec. 22, 2011, 7 pages.
ISR and Written Opinion in PCT/US2011/48452, dated Dec. 22, 2011, 7 pages.
Johne, et al., *Staphylococcus aureus* exopolysaccharide in vivo demonstrated by immunomagnetic separation and electron microscopy, J. Clin. Microbiol. 27:1631-1635 (1989).
Johnson, Thermal Agitation of Electricity in Conductors, Phys. Rev., 32:97-109 (1928).
Kaittanis, et al., One-step nanoparticle mediated bacterial detection with magentic relaxation, Nano Lett., 7(2):381-383 (2007).
Klaschik, S., L. E. Lehmann, et al. (2002). "Real-time PCR for detection and differentiation of gram-positive and gram-negative bacteria." J Clin Microbiol 40(11): 4304-4307.
Kleinstruer, "Microfluidics and Nanofluidics: Theory and Selected Applications," John Wiley & Sons, 2013.
Lecomte et al. Nucl Acids Res. 11:7505 (1983).
Lee, et al., Chip-NRM Biosensor for detection and molecular analysis of cells, Nature Medicine, 14(8):869-874 (2008).
Levin, Cell 88:5-8 (1997).
Li et al., 2010, Chemiluminescent Detect of *E. coli* O157:H7 Using Immunological Method Based on Magnetic Nanoparticles, J. of Nanoscience and Nanotechnology 10:696-701.
Life Technologies, "Dynabeads® for Immunoassay IVD", retrieved from http://www.invitrogen.com/site/us/en/home/Productsand-Services/Applications/Diagnostics-Clinical-Research/Bead-based-IVD-Assays/Bead-based-1 mmunoassay-IVD.html on May 29, 2013, four pages.
Lu et al., 2007, Magnetic Nanoparticles: Synthesis, Protection, Functionalization, and Application, Angew. Chem. Int. Ed. 46:1222-1244.
Lund, et al., Immunomagnetic separation and DNA hybridization for detection of enterotoxigenic *Escherichia coli* in a piglet model, J. Clin. Microbiol., 29:2259-2262 (1991).
Madonna A J, et al. "Detection of Bacteria from Biological Mixtures Using Immunomagnetic Separation Combined with Matrix-Assisted Laser Desorption/Ionization Time-of-flight Mass Spectrometry", Rapid Communications in Mass Spectrometry, John WIley & Sons, GB, vol. 15, No. 13, Jan. 1, 2001, pp. 1068-1074.
Magin, et al., Miniature Magnetic Resonance Machines, IEEE Spectrum 34(10):51-61 (1997).
Malba, et al., Laser-lathe Lithography—A Novel Method for Manufacturing Nuclear Magnetic Resonance Microcoils, Biomed. Microdev., 5:21-27 (2003).
Maniatis et al., Molecular Cloning: A Laboratory Manual, 1982, Cold Spring Harbor, NY, pp. 280-281.
Margin, et al., High resolution microcoil 1H-NMR for mass-limited, nanoliter-volume samples, Science, 270:1967 (1995).
Margulies et al., Nature, 437: 376-380 (2005).
Massin, et al., Planar Microcoil-based magnetic resonance imaging of cells, Transducers '03, The 12th Int. Conf. on Solid State Sensors, Actuators, and Microsystems, Boston, Jun. 8-12, pp. 967-970 (2003).
Massin, et al., Planar Microcoil-based Microfluidic Nmr Probes, J. Magn. Reson., 164:242-255 (2003).
Matar et al., 1990, Magnetic particles derived from iron nitride, IEEE Transactions on magnetics 26(1):60-62.
McDowell, et al., Operating Nanoliter Scale Nmr Microcoils in a Itesla Field, J. Mag. Reson., 188(1):74-82 (2007).
Minard, et al., Solenoidal Microcoil Design, Part I: Optimizing RF Homogeneity and coil dimensions, Concepts in Magn. Reson., 13(2):128-142 (2001).
Moreira et al., 2008, Detection of Salmonella Typhimurium in Raw Meats using In-House Prepared Monoclonal Antibody Coated Magnetic Beads and Pcr Assay of the fimA Gene. Journal of Immunoassay & Immunochemistry 29:58-69.
Moresi and Magin, Miniature Permanent Magnet for Table-top NMR, Concept. Magn. Res., 19B:35-43 (2003).
Moudrianakis et al., Proc. Natl. Acad. Sci. 53:564-71 (1965).
Mulder, et al., Characterization of two human monoclonal antibodies reactive with HLA-B12 and HLA-B60, respectively, raised by in vitro secondary immunization of peripheral blood lymphocytes, Hum. Immunol., 36(3):186-192 (1993).
Myers and Gelfand, Biochemistry 30:7661 (1991).
Narang et al., Methods Enzymol., 68:90 (1979).
Nordstrom et al., J. Biol. Chem. 256:3112 (1981).
Nyquist, Thermal Agitation of Electrical Charge in Conductors, Phys. Rev., 32:110-113 (1928).

(56) References Cited

OTHER PUBLICATIONS

Ohno et al, 2011, Effects of Blood Group Antigen-Binding Adhesin Expression during Helicobacter pylori Infection of Mongolian Gerbils, The Journal of Infectious Diseases 203:726-735.
Olson, et al., High-resolution microcoil NMR for analysis of mass-limited, nanoliter samples, Anal. Chem., 70:645-650 (1998).
Olsvik_et_al_Magnetic_Seperation_Techniques_in_Diagnostic_Microbiology_Clinical_Microbiol_Rev_1994_7_43_54.
Pappas, et al., Cellular Separations: A Review of New Challenges in Analytical Chemistry, Analytica Chimica Acta, 601(1):26-35 (2007).
Peck, et al., Design and Analysis of Microcoils for NMR Microscopy, J. Magn. Reson. B 108:114-124 (1995).
Peck, et al., RF Microcoils patterned using microlithographic techniques for use as microsensors in NMR, Proc. 15th Ann. Int. Conf. of the IEEE, Oct. 28-31, pp. 174-175 (1993).
Perez, et al., Viral-induced self-assembly of magnetic nanoparticle allows detection of viral particles in biological media, J. Am. Chem. Soc., 125:10192-10193 (2003).
Qiu, et al., Immunomagnetic separation and rapid detection of bacteria using bioluminescence and microfluidics, Talanta, 79:787-795 (2009).
Rogers, et al., Using microcontact printing to fabricate microcoils on capillaries for high resolution proton nuclear magnetic resonance on nanoliter volumes, Appl. Phys. Lett., 70:2464-2466 (1997).
Safarik et al., "The application of magnetic separations in applied Microbiology" Journal of Applied Bacteriology 1995, 78, 575-585.
Sambrook and Russell, Molecular Cloning: A Laboratory Manual 3Ed, Cold Spring Harbor Laboratory Press, 2001.
Seeber, et al., Design and Testing of high sensitivity Microreceiver Coil Apparatus for Nuclear Magnetic Resonance and Imaging, Rev. Sci. Inst., 72:2171-2179 (2001).
Seeber, et al., Triaxial Magnetic Field Gradient System for Microcoil Magnetic Resonance Imaging, Rev. Sci. Inst., 71:4263-4272 (2000).
Sillerud, et al., 1H NMR Detection of Superparamagnetic Nanoparticles at 1 T using a Microcoil and Novel Tuning Circuit, J. Magn. Reson. 181:181-190 (2006).
Sista et al., 2008, Heterogeneous Immunoassays Using Magnetic beads on a Digital Microfluidic Platform, Lab Chip 8(2):2188-2196.
Skjerve, et al., Detection of Listeria monocytogenes in foods by immunomagnetic separation, Appl. Env. Microbiol., 56:3478 (1990).
Soni et al., Clin Chem 53:1996-2001 (2007).
Sorli, et al., Micro-spectrometer for NMR: analysis of small quantities in vitro, Meas. Sci. Technol., 15:877-880 (2004).
Stanley, Essentials in Immunology and Serology, Delmar, pp. 153-153 (2002).
Stauber, et al., Rapid generation of monoclonal antibody-secreting hybridomas against African horse sickness virus by in vitro immunization and the fusion/cloning technique, J. Immunol. Methods, 161(2):157-168 (1993).
Stenesh and McGowan, Biochim Biophys Acta, 475:32 (1977).
Stocker, et al., Nanoliter volume, high-resolution Nmr Microspectroscopy using a 60 um planer microcoil, IEEE Trans. Biomed. Eng., 44:1122-1127 (1997).
Subramanian, et al., RF Microcoil Design for Practical NMR of Mass-Limited Samples, J. Magn. Reson., 133:227-231 (1998).
Takagi et al., Appl. Environ. Microbiol. 63:4504 (1997).
Taktak, et al., Multiparameter Magnetic Relaxation Switch Assays, Analytical Chemistry, 79(23):8863-8869 (2007).
The United States Naval Research Laboratory (Nrl), "The Fabs Device: Magnetic Particles", retrieved from http://www.nrl.navy.mil/chemistry/6170/6177/beads.php on Jan. 8, 2013, two pages.
Torensama, et al., Monoclonal Antibodies Specific for the Phase-Variant O-Acetylated Ki Capsule of Escerichia coli, J. Clin. Microbiol., 29(7):1356-1358 (1991).
Trumbull, et al., Integrating microfabricated fluidic systems and NMR spectroscopy, IEEE Trans. Biomed. Eng., 47(1):3-7 (2000).
Van Bentum, et al., Towards Nuclear Magnetic Resonance (MU)-Spectroscopy and (MU)-Imaging, Analyst, Royal Society of Chemistry, London, 129(9):793-803 (2004).
Vandeventer, J. Clin. Microbiol. Jul 2011, 49(7):2533-39.
Venkateswaran, et al., Production of Anti-Fibroblast Growth Factor Receptor Monoclonal Antibodies by in Vitro Immunization, Hybridoma, 11(6):729-739 (1992).
Verma, Biochim Biophys Acta. 473:1-38 (1977).
Vermunt, et al., Isolation of salmonelas by immunomagnetic separation, J. Appl. Bact., 72:112-118 (1992).
Wang and Irudayaraj, Multifunctional Magnetic-Optical Nanoparticle Probes for Simultaneous Detection, Separation, and Thermal Ablation of Multiple Pathogens, Small, 6(2):283-289 (2010).
Webb and Grant, Signal-to-Noise and Magnetic Susceptibility Tradeoffs in Solenoidal Microcoils for NMR, J. Magn. Reson. B, 113:83-87 (1996).
Wensink, et al., High Signal to Noise Ratio in Low-field NMR on a Chip: Simulations and Experimental Results, 17th IEEE MEMS, 407-410 (2004).
Williams and Wang, Microfabrication of an electromagnetic power micro-relay using SU-8 based UV-LIGA technology, Microsystem Technologies, 10(10):699-705 (2004).
Wu, et al., 1H-NMR Spectroscopy on the Nanoliter Scale for Static and On-Line Measurements, Anal. Chem., 66:3849 (1994).
Yeung et al., 2002, Quantitative Screening of Yeast Surface-Displayed Polypeptide Libraries by Magnetic Bead Capture. Biotechnol. 18:212-220.
Yu et al. "Development of a Magnetic Microplate Chemifluorimmunoassay for Rapid Detection of Bacteria and Toxin in Blood", Analytical Biochemistry 261 (1998), pp. 1-7.
Zhao, et al., A rapid bioassay for single bacterial cell quantitation using bioconjugated nanoparticles, PNAS, 101(42):15027-15032 (2004).
Zordan, et al., Detection of Pathogenic E. coli O157:H7 by a Hybrid Microfluidic SPR and Molecular Imaging Cytometry Device, Cytometry A, 75A:155-162 (2009).
Harlow, et al., 1988, 'Antibodies', Cold Spring Harbor Laboratory, pp. 93-117.
Hongwei Gu et al: : Using Biofunctional Magnetic Nanoparticles to Capture Vancomycin-Resistent Enterococci and Other Gram-Positive Bacteria at Ultralow Concentration, Journal of the American Chemical Society, vol. 125, No. 51, Dec. 1, 2003 (Dec. 1, 2003), pp. 15702-15703, XP055087066, ISSN; 002-7863, DOI: 10.1021/ja0359310.
Hunter, et al.. Immunoassays for Clinical Chemistry, pp. 147-162, Churchill Livingston, Edinborough (1983).
International Search Report for PCT/US2013/076649 with an International filing dated Dec. 19, 2013, 2 pages.
IPRP in PCT/US2008/058518, dated Jul. 7, 2008, 21 pages.
ISR and Written Opinion in PCT/US2008/058518, dated Jul. 7, 2008, 15 pages.
Life Technologies, "Dynabeads® for Immunoassay IVD", retrieved from http://www.invitrogen.com/site/us/en/home/Productsand-Services/Applications/Diagnostics-Clinical-Research/Bead-based-IVD-Assays/Bead-based-Immunoassay-IVD.html on May 29, 2013, four pages.
Massin, et al., Planar Microcoil-based magnetic resonance imaging of cells, Transducers '03, The 12th Int. Conf. on Solid State Sensors, Actuators, and Microsystems, Boston, June 8-12, pp. 967-970 (2003).
Miltenyi Biotec, 2007, "autoMACS™ Pro Separator", 13/0972-7-91.02, 2007, 8 pages.
NCBI Geo Gene Expression Omnibus, Entry for GSE22885, retrieved from https://www.nobi.nlm.nih.gov/geo/query/acc.cgi?aco=GSE22885 on May 25, 2017, with excerpts of files GPL10672_IMS_annotation.ann.txt.gz and GSM565264.txt.gz therein (five pages total), publicly available on Jul. 13, 2010 (5 Pages).
Payne, M.J. et al., "The Use of Immobilized Lectins in the Separation of Staphylococcus aureus, Escherichia coli, Listeria and Salmonella spp. from Pure Cultures and Foods", Journal of Applied Bacteriology, 1992, No. 73, pp. 41-52 (12 Pages).
The United States Naval Research Laboratory (NRL), "The FABS Device: Magnetic Particles", retrieved from http://vww.nrl.navy.mil/chemistry/6170/6177/beads.php on Jan. 8, 2013, two pages.

(56) References Cited

OTHER PUBLICATIONS

Wang et al, 2010, Multifunctional Magnetic-Optical Nanoparticle Probes for Simultaneous Detection, Separation, and Thermal Ablation of Multiple Pathogens, SMALL 6(2):283-289.
Wang et al., 2010, Separation and detection of multiple pathogens in a food matrix by magnetic SERS nanoprobes, Analytical and Bioanalytical Chemistry, 399(3):1271-1278.
Agrawal et al., 1990, Tetrahedron Letters 31:1543-46.
Andreassen, Jack, "One micron magnetic beads optimised for automated immunoassays" as Published in CLI Apr. 2005, retrieved from http://www.cli-online.com/uploads/tx_ttproducts/datasheet/one-micron-magnetic-beads-optimised-for-automatedimmunoassays.pdf on Dec. 28, 2015, four pages.
Armenean, et al., NMR Radiofrequency Microcoil Design: Electromagnetic Simulation Usefulness, Compes Rendus Biologies, 325(4):457-463 (2002).
Armenean, et al., Solenoidal and Planar Microcoils for NMR Spectroscopy, Proc. of the 25th Annual Int Conf. of the IEEE Eng. in Med. and Bio. Soc., Cancun, Mexico, Sep. 17, 2003, pp. 3045-3048.
Barany et al., Gene, 108:1 (1991).
Barany F. (1991) PNAS 88:189-193.
Barany, F., Genome research, 1:5-16 (1991).
Braslavsky et al., PNAS, 100:3690-3694 (2003).
Bruno et al., 1996, Development of an Immunomagnetic Assay System for Rapid Detection of Bacteria and Leukocytes in Body Fluids, Journal of Molecular Recognition 9(5):474-479.
Chandler et al., 2001, Automated immunomagnetic separation and microarray detection of *E. coli* O157:H7 from poultry carcass rinse, International Journal of Food Microbiology 70(1-2):143-154.
Cheng et al., 2012, Concentralion and detection of bacteria in virtual environmental samples based on non-immunomagnetic separation and quantum dots by using a laboratory-made system, Proc. of SPIE:82310Y-1-82310Y-18.
Extended European Search Report dated Aug. 20, 2014, for EP Application No. 11864030.9 (7 pages).
Extended European Search Report dated Feb. 2, 2017 for European Application No. 16190239.0 (8 Pages).
Furdui, Vasile I. et al., "Immunomagnetic T Cell Capture From Blood for PCR Analysis Using Microfluidic Systems", Lab on a Chip, 2004, vol. 4 No. 6, pp. 614-618 (5 Pages).
Furdui, Vasile I. et al., "Microfabricated Electrolysis Pump System for Isolating Rare Cells in Blood; Micro-Electrolysis Pumps for Blood", Journal of Micromechanics & Microengineering, vol. 13, No. 4, Jul. 1, 2003, pp. S164-S170 (7 Pages).
Gesbert et al. "Asparagine Assimilation is Critical for Intracellular Replication and Dissemination of Francisella" Cellular Microbiology, 2014, 16(3), pp. 434-449 (16 Pages).
Wang Hong, Ph.D., "Rapid and Simultaneous Detection of Foodborne Bacterial Pathogens Using Multiplex Assays", Dissertation Abstract, University of Arkansas, 2010 (2 Pages).
Yang et al., "Simultaneous Detection of *Escherichia coli* O157:H7 and *Salmonella typhimurium* Using Quantum Dots as Fluorescence Labels", Analyst 131(3), Mar. 2006, pp. 394-101 (8 Pages).

\* cited by examiner

METHODS FOR RAISING ANTIBODIES

RELATED APPLICATIONS

The present application is a continuation of U.S. nonprovisional application Ser. No. 14/132,099, filed Dec. 18, 2013 and now issued as U.S. Pat. No. 10,000,557, which claims the benefit of and priority to U.S. provisional patent application Ser. No. 61/739,511 filed Dec. 19, 2012, the content of which is incorporated by reference herein in its entirety.

FIELD OF THE INVENTION

The present invention generally relates to methods of generating antibodies against a species of pathogen that involve identifying the pathogen that is most genetically representative of the members of pathogen species and using the identified pathogen to generate an antibody.

BACKGROUND

Sepsis is a leading cause of death in the United States. During sepsis, the body undergoes a severe inflammatory response to infection. Early detection of the blood-borne pathogens underlying the infection remains crucial to preventing the onset of sepsis. Traditional methods of detection and identification of these pathogens often involve the use of antibodies specific for the pathogen of interest in immune-based assays.

Development of antibodies that efficiently and reliably capture particular pathogen species from biological matrices, such as blood, is complicated by the large number of strain types, often with markedly different antigenic properties (serotypes), which can exist within a species. Antibodies raised against a single index strain of species may not cross-react with other isolates, or strains of the same species. Accordingly, the development of an antibody that can be used against a wide variety of strains is problematic.

One possible solution would be to inoculate against all, or nearly all, of the known different strain-types and combine the antibodies. This, however, would require inoculation of hundreds of animals with individual pathogen strains. Combining isolates within the inoculation medium may reduce the number of animals required, however, a large number of animals is still necessary to cover combinations of all the known serotypes.

Another strategy would be to determine the minimal subset of strains that would represent most, or all, of the antigenic variations across a species. For some species, data regarding the known antigenic variation across the species is available, as well as the relative abundance of the antigenic variants, i.e., the serotypes, in different diseases or environments. However, such information does not exist for most species, indicating a need for alternate methods of developing antibodies that can be used across antigenic variants.

SUMMARY

The present invention provides methods for employing genotyping to assess genomic variations across different species as a means of selecting a minimal subset of isolates to be used as immunogens to generate antibodies that interact with most, or all, of the clinically-important strains of each species. Using genomic information, a minimal subset of strains to represent most, or all, of the antigenic variation across a species is determined.

The present invention provides methods for generating antibodies by using genotyping to survey the extent of genetic variation within a species The provided method then groups genomically-similar isolates together, such that one isolate from a group of closely related strains may be used to represent the entire species within the group. The groupings then serve as guides for selection of a minimal subset of strains representative of the spectrum of genomic variation existing within each species. An isolate from each group is then used in the production of antibodies, where based upon the genetic similarities within a group, the selected isolate would produce an immunological response in antibody production to cover the identified strains with a group. Therefore, by having several groups of genetically similar strains and selecting one isolate from each group, a panel of isolates is selected that would be used in antibody production.

Rather than assessing antigenic variation, methods of the present invention involve the use of genotyping to assess genomic variation across different species as a means of selecting a minimal subset of isolates to be used as antigens for the generation of antibodies able to interact with most, or all, of the clinically-important strains of each species. Accordingly, the present methods may facilitate the generation of broad specificity antibodies across most, or all, antigenic variants within clinically or industrially important microbial species and further facilitate the development of new antibody-based analytical methods.

In certain aspects, the invention provides a method for generating antibodies against a species of pathogen. The method involves obtaining a nucleic acid from a plurality of pathogens within the same species and comparing the obtained nucleic acids for genetic similarities. The method further includes grouping the pathogens based upon genomic similarities and then identifying the smallest subset of pathogens representative of the species based on the comparison and using the identified subset to generate an antibody. For example, the plurality of pathogens could be grouped so that each group is 97% similar in genomes. Then, from each group, a single pathogen is selected to represent the group in antibody production. Therefore, this small subset of pathogens would be used in antibody production. The subset would represent most, or all, clinically relevant strains of the species. Accordingly, a set of antibodies would be produced that can bind most or all of the clinically relevant strains of a species.

Any method for analyzing pathogen genomes is suitable for use with the provided methods. Such methods would be used to assess the level of similarity and/or dissimilarity of different pathogen isolates. The methods include, without limitation, ribotyping, rep-PCR, pulsed-field gel electrophoresis, optical mapping, microarray-based measurements of single-nucleotide polymorphisms, or any combination of these. These methods may also be used to assess the range of genetic variation across or within pathogen species and for the building of "similarity trees" or "cladograms," in which genomically similar strains are grouped together to form branches or "clades." These groupings can be used to guide selection of the smallest subset of strains that still represent the breadth of genomic variation within the species.

Methods of the present invention are suitable for developing both monoclonal and polyclonal antibodies. Monoclonal antibodies refer to antibody molecules of singular epitope specificity originally produced by one B-cell and sharing identical sequence. Polyclonal antibodies, on the other hand, refer to antibody molecules which differ in their epitope binding and complementarity region amino acid sequence but share an overall target specificity. Methods of the present invention can be used to generate monoclonal antibodies when, for example, the smallest representative subset is a single strain of bacteria featuring an epitope found on all strains. The provided methods are useful for generating polyclonal antibodies when the smallest representative subset includes a number of strains encompassing a host of epitopes.

Although the present methods are useful for developing antibodies against any type of pathogen, they are particularly suited for developing antibodies against bacteria, which are known to encompass a wide range of strains within a single species. Such bacteria may include gram positive bacteria or gram negative bacteria. Exemplary bacterial species that may be used in conjunction with the provided methods include, but are not limited to *E. coli, Listeria, Clostridium, Mycobacterium, Shigella, Borrelia, Campylobacter, Bacillus, Salmonella, Staphylococcus, Enterococcus, Pneumococcus*, and *Streptococcus*.

Additional aspects of the invention will become apparent upon review of the following disclosure.

DETAILED DESCRIPTION

The invention generally relates to methods for generating a set of antibodies that can bind most or all clinically relevant strains within a given species of pathogen. The provided methods use genotyping to survey the extent of genetic variation within a species. The provided method groups genomically-similar isolates together, such that one isolate from a group of closely related strains may be used to represent the entire species, and uses the groupings to guide selection of a minimal subset of strains representative of the spectrum of genomic variation existing within each species. In one aspect of the invention, pathogens identified as the minimal subset of strains are then used in the production and development of antibodies.

Genotyping

As encompassed by the invention genotyping may require the isolation of nucleic acids from a sample, such as a bacterial pathogen. Genotyping, or the process of determining differences in the genetic make-up (genotype) of a species in the sample, is accomplished by examining the species' DNA sequence using biological assays and comparing it to another similar species' sequence or a reference sequence that may or may not be present in the sample. Traditionally genotyping is the use of DNA sequences to define biological populations by analyzing for genetic similarities and differences. Current methods of genotyping known in the art include restriction fragment length polymorphism identification (RFLPI) of genomic DNA, random amplified polymorphic detection (RAPD) of genomic DNA, amplified fragment length polymorphism detection (AFLPD), polymerase chain reaction (PCR), DNA sequencing, allele specific oligonucleotide (ASO) probes, and hybridization to DNA microarrays or beads. Genotyping applies to a broad range of species, including pathogens, microorganisms, viruses, and bacteria.

For genotyping, nucleic acids from the species need to be isolated. Nucleic acid in a sample can be any nucleic acid, including for example, genomic DNA in a tissue sample, cDNA amplified from a particular target in a laboratory sample, or mixed DNA from multiple organisms. In some embodiments, the sample includes homozygous DNA from a haploid or diploid organism. For example, a sample can include genomic DNA from a patient who is homozygous for a rare recessive allele. In other embodiments, the sample includes heterozygous genetic material from a diploid or polyploidy organism with a somatic mutation such that two related nucleic acids are present in allele frequencies other than 50 or 100%, i.e., 20%, 5%, 1%, 0.1%, or any other allele frequency.

Samples

In one embodiment, nucleic acid template molecules (e.g., DNA or RNA) are isolated from a biological sample containing a variety of other components, such as proteins, lipids, and non-template nucleic acids. Nucleic acid template molecules can be obtained from any cellular material, obtained from animal, plant, bacterium, fungus, or any other cellular organism. Biological samples for use in the present invention also include viral particles or preparations. Nucleic acid template molecules can be obtained directly from an organism or from a biological sample obtained from an organism, e.g., from blood, urine, cerebrospinal fluid, seminal fluid, saliva, sputum, stool, and tissue. Any tissue or body fluid specimen may be used as a source for nucleic acid to use in the invention. Nucleic acid template molecules can also be isolated from cultured cells, such as a primary cell culture or cell line. The cells or tissues from which template nucleic acids are obtained can be infected with a virus or other intracellular pathogen. A sample can also be total RNA extracted from a biological specimen, a cDNA library, viral, or genomic DNA. A sample may also be isolated DNA from a non-cellular origin, e.g. amplified/isolated DNA from the freezer.

Generally, nucleic acid can be extracted from a biological sample by a variety of techniques such as those described by Maniatis, et al., Molecular Cloning: A Laboratory Manual, 1982, Cold Spring Harbor, N.Y., pp. 280-281; Sambrook and Russell, Molecular Cloning: A Laboratory Manual 3Ed, Cold Spring Harbor Laboratory Press, 2001, Cold Spring Harbor, N.Y.; or as described in U.S. Pub. 2002/01900663.

Nucleic acid obtained from biological samples may be fragmented to produce suitable fragments for analysis. Template nucleic acids may be fragmented or sheared to a desired length, using a variety of mechanical, chemical, and/or enzymatic methods. DNA may be randomly sheared via sonication, e.g. Covaris method, brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA. If fragmentation is employed, the RNA may be converted to cDNA before or after fragmentation. In one embodiment, nucleic acid is fragmented by sonication. In another embodiment, nucleic acid is fragmented by a hydroshear instrument. Generally, individual nucleic acid template molecules can be from about 2 kb bases to about 40 kb. In a particular embodiment, nucleic acids are about 6 kb-10 kb fragments. Nucleic acid molecules may be single-stranded, double-stranded, or double stranded with single-stranded regions (for example, stem- and loop-structures).

A biological sample as described herein may be homogenized or fractionated in the presence of a detergent or surfactant. The concentration of the detergent in the buffer may be about 0.05% to about 10.0%. The concentration of the detergent can be up to an amount where the detergent remains soluble in the solution. In one embodiment, the concentration of the detergent is between 0.1% to about 2%. The detergent, particularly one that is mild and nondenaturing, can act to solubilize the sample. Detergents may be ionic or nonionic. Examples of nonionic detergents include triton, such as the TRITON X series (Triton X-100 t-Oct- $C_6H_4$—$(OCH_2$—$CH_2)_xOH$, x=9-10, (surfactant, commercially available by the Dow Chemical Company), TRITON X-100R, (surfactant, commercially available by the Dow Chemical Company), TRITON X-114 x=7-8) (surfactant, commercially available by the Dow Chemical Company), octyl glucoside, polyoxyethylene(9)dodecyl ether, digitonin, IGEPAL IGEPAL (surfactant, commercially available by Sigma-Aldrich, Inc.), CA630 octylphenyl polyethylene glycol, n-octyl-beta-D-glucopyranoside (betaOG), n-dodecyl-beta, Tween 20 polyethylene glycol sorbitan monolaurate, Tween 80 polyethylene glycol sorbitan monooleate, polidocanol, n-dodecyl beta-D-maltoside (DDM), NP-40 non-ylphenyl polyethylene glycol, C12E8 (octaethylene glycol n-dodecyl monoether), hexaethyleneglycol mono-n-tetradecyl ether (C14E06), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl) dimethyl-ammonio]-1-propanesulfonate. It is contemplated also that urea may be added with or without another detergent or surfactant.

Lysing

Lysis or homogenization solutions may further contain other agents, such as reducing agents. Examples of such reducing agents include dithiothretol (DTT), β-mercaptoethanol, DTE, GSH, cysteine, cystemine, tricarboxyethyl phosphine (TCEP), or salts of sulfurous acid. Any lysis procedure known in the art may be used to lyse the target. Exemplary methods include enzymatic methods (such as lysozyme, mutanolysin and proteinase K), mechanical methods, thermal methods, chemical methods, or a combination thereof. Exemplary mechanical methods include sonication (i.e., sonic oscillation), bead beating (Vandeventer, J Clin Microbiol. 2011 July; 49(7):2533-9), and liquid homogenization (shearing by forcing the target them through a narrow space). Chemical methods, buffers and combinations of detergents, such as nonionic detergent, can also be employed. Generally, lysis buffers contain alkali (such as NaOH), guanidine salts (such as guanidine thiocyanate), tris-HCl, EDTA, EGTA, SDS, deoxycholate, tritonX and/or NP-40. In some cases the buffer may also contain NaCl (150 mM). An exemplary chemical lysis buffer is (7 M urea, 2 M thiourea, 4% (w/v) 3-[(3-cholamidopropyl)dimethylammonio]-1-propanesulfonate (CHAPS), 65 mM dithiothreitol (DTT), and 1% (v/v) protease inhibitor at −80° C.). Other such buffers are known in the art and are commercially available.

In particular embodiments, the species (such as a pathogen or bacteria) is lysed using thermal methods. In thermal lysis, the species is heated to about 90° C., about 95° C., about 100° C., etc., causing the species (such as a pathogen or bacteria) to lyse. Thermal lysis procedures are described for example in Privorotskaya et al. (Lab Chip. 2010 May 7; 10(9):1135-41) and Kim et al. (Journal of Nanoscience and Nanotechnology, Vol. 9, 2841-2845, 2009), the content of each of which is incorporated by reference herein in its entirety. Application of heat not only lyses the species, it also denatures the released double stranded nucleic acid into single stranded nucleic acid and initiates the amplification reaction. Another advantage of thermal lysis is that the heat facilitates denaturation/inactivation of nucleases that can cause degradation of nucleic acid.

After lysis, an amplification reaction is conducted on the nucleic acid released form the species.

Amplification

In various embodiments, the nucleic acid is amplified, for example, from the sample or after isolation from the sample. Amplification refers to production of additional copies of a nucleic acid sequence and is generally conducted using polymerase chain reaction (PCR) or other technologies well-known in the art (e.g., Dieffenbach and Dveksler, PCR Primer, a Laboratory Manual, 1995, Cold Spring Harbor Press, Plainview, N.Y.). The amplification reaction may be any amplification reaction known in the art that amplifies nucleic acid molecules, such as polymerase chain reaction, nested polymerase chain reaction, polymerase chain reaction-single strand conformation polymorphism, ligase chain reaction (Barany, F. Genome research, 1:5-16 (1991); Barany, F., PNAS, 88:189-193 (1991); U.S. Pat. Nos. 5,869, 252; and 6,100,099), strand displacement amplification and restriction fragment length polymorphism, transcription based amplification system, rolling circle amplification, and hyper-branched rolling circle amplification. Further examples of amplification techniques that can be used include, without limitation, quantitative PCR, quantitative fluorescent PCR (QF-PCR), multiplex fluorescent PCR (MF-PCR), real time PCR (RTPCR), single cell PCR, restriction fragment length polymorphism (PCR-RFLP), RT-PCR-RFLP, hot start PCR, in situ polonony PCR, in situ rolling circle amplification (RCA), bridge PCR, picotiter PCR, and emulsion PCR. Other suitable amplification methods include transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938.

In certain embodiments, the amplification reaction is the polymerase chain reaction. Polymerase chain reaction refers to methods by K. B. Mullis (U.S. Pat. Nos. 4,683,195 and 4,683,202, hereby incorporated by reference) for increasing concentration of a segment of a target sequence in a mixture of genomic DNA without cloning or purification.

Primers can be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. Also, the annealing position of each primer pair can be designed such that the sequence and length of the primer pairs yield the desired melting temperature. The simplest equation for determining the melting temperature of primers smaller than 25 base pairs is the Wallace Rule (Td=2(A+T)+4(G+C)). Computer programs can also be used to design primers, including but not limited to Array Designer Software from Arrayit Corporation (Sunnyvale, Calif.), Oligonucleotide Probe Sequence Design Software for Genetic Analysis from Olympus Optical Co., Ltd. (Tokyo, Japan), NetPrimer, and DNAsis Max v3.0 from Hitachi Solutions America, Ltd. (South San Francisco, Calif.). The TM (melting or annealing temperature) of each primer is calculated using software programs such as OligoAnalyzer 3.1, available on the web site of Integrated DNA Technologies, Inc. (Coralville, Iowa).

With PCR, it is possible to amplify a single copy of a specific target sequence in genomic DNA to a level that can be detected by several different methodologies (e.g., staining; hybridization with a labeled probe; incorporation of biotinylated primers followed by avidin-enzyme conjugate detection; or incorporation of 32P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

Amplification adapters may be attached to the fragmented nucleic acid. Adapters may be commercially obtained, such as from Integrated DNA Technologies (Coralville, Iowa). In certain embodiments, the adapter sequences are attached to the template nucleic acid molecule with an enzyme. The enzyme may be a ligase or a polymerase. The ligase may be any enzyme capable of ligating an oligonucleotide (RNA or DNA) to the template nucleic acid molecule. Suitable ligases include T4 DNA ligase and T4 RNA ligase, available commercially from New England Biolabs (Ipswich, Mass.). Methods for using ligases are well known in the art. The polymerase may be any enzyme capable of adding nucleotides to the 3' and the 5' terminus of template nucleic acid molecules.

The ligation may be blunt ended or utilize complementary overhanging ends. In certain embodiments, the ends of the fragments may be repaired, trimmed (e.g. using an exonuclease), or filled (e.g., using a polymerase and dNTPs) following fragmentation to form blunt ends. In some embodiments, end repair is performed to generate blunt end 5' phosphorylated nucleic acid ends using commercial kits, such as those available from Epicentre Biotechnologies (Madison, Wis.). Upon generating blunt ends, the ends may be treated with a polymerase and dATP to form a template independent addition to the 3'-end and the 5'-end of the fragments, thus producing a single A overhanging. This single A is used to guide ligation of fragments with a single T overhanging from the 5'-end in a method referred to as T-A cloning.

Alternatively, because the possible combination of overhangs left by the restriction enzymes are known after a restriction digestion, the ends may be left as-is, i.e., ragged ends. In certain embodiments double stranded oligonucleotides with complementary overhanging ends are used.

In certain embodiments, a single bar code is attached to each fragment. In other embodiments, a plurality of bar codes, e.g., two bar codes, are attached to each fragment. A bar code sequence generally includes certain features that make the sequence useful in sequencing reactions. For example the bar code sequences are designed to have minimal or no homopolymer regions, i.e., 2 or more of the same base in a row such as AA or CCC, within the bar code sequence. The bar code sequences are also designed so that they are at least one edit distance away from the base addition order when performing base-by-base sequencing, ensuring that the first and last base do not match the expected bases of the sequence.

The bar code sequences are designed such that each sequence is correlated to a particular portion of nucleic acid, allowing sequence reads to be correlated back to the portion from which they came. Methods of designing sets of bar code sequences are shown for example in U.S. Pat. No. 6,235,475, the contents of which are incorporated by reference herein in their entirety. In certain embodiments, the bar code sequences range from about 5 nucleotides to about 15 nucleotides. In a particular embodiment, the bar code sequences range from about 4 nucleotides to about 7 nucleotides. Since the bar code sequence is sequenced along with the template nucleic acid, the oligonucleotide length should be of minimal length so as to permit the longest read from the template nucleic acid attached. Generally, the bar code sequences are spaced from the template nucleic acid molecule by at least one base (minimizes homopolymeric combinations).

Embodiments of the invention involve attaching the bar code sequences to the template nucleic acids. In certain embodiments, the bar code sequences are attached to the template nucleic acid molecule with an enzyme. The enzyme may be a ligase or a polymerase, as discussed above. Attaching bar code sequences to nucleic acid templates is shown in U.S. Pub. 2008/0081330 and U.S. Pub. 2011/0301042, the contents of which are incorporated by reference herein in its entirety. Methods for designing sets of bar code sequences and other methods for attaching bar code sequences are shown in U.S. Pat. Nos. 6,138,077; 6,352,828; 5,636,400; 6,172,214; 6,235,475; 7,393,665; 7,544,473; 5,846,719; 5,695,934; 5,604,097; 6,150,516; RE39,793; 7,537,897; 6,172,218; and 5,863,722, the content of each of which is incorporated by reference herein in its entirety.

Sequencing

After any of the aforementioned processing steps (e.g., obtaining, isolating, fragmenting, or amplification), nucleic acid can be sequenced to generate a plurality of sequence reads, according to certain embodiments of the invention.

Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of separated molecules has more recently been demonstrated by sequential or single extension reactions using polymerases or ligases as well as by single or sequential differential hybridizations with libraries of probes.

A sequencing technique that can be used in the methods of the provided invention includes, for example, 454 sequencing (454 Life Sciences, a Roche company, Branford, Conn.) (Margulies, M et al., Nature, 437:376-380 (2005); U.S. Pat. Nos. 5,583,024; 5,674,713; and 5,700,673). 454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used in the methods of the provided invention is SOLiD technology by Applied Biosystems from Life Technologies Corporation (Carlsbad, Calif.). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

Another example of a DNA sequencing technique that can be used in the methods of the provided invention is Ion Torrent sequencing, described, for example, in U.S. Pubs. 2009/0026082, 2009/0127589, 2010/0035252, 2010/0137143, 2010/0188073, 2010/0197507, 2010/0282617, 2010/0300559, 2010/0300895, 2010/0301398, and 2010/0304982, the content of each of which is incorporated by reference herein in its entirety. In Ion Torrent sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and are attached at a resolution such that the fragments are individually resolvable. Addition of one or more nucleotides releases a proton ($H^+$), which signal is detected and recorded in a sequencing instrument. The signal strength is proportional to the number of nucleotides incorporated.

Another example of a sequencing technology that can be used in the methods of the provided invention is Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated. Sequencing according to this technology is described in U.S. Pub. 2011/0009278, U.S. Pub. 2007/0114362, U.S. Pub. 2006/0024681, U.S. Pub. 2006/0292611, U.S. Pat. Nos. 7,960,120, 7,835,871, 7,232,656, 7,598,035, 6,306,597, 6,210,891, 6,828,100, 6,833,246, and 6,911,345, the contents of which are herein incorporated by reference in their entirety.

Another example of a sequencing technology that can be used in the methods of the provided invention includes the single molecule, real-time (SMRT) technology of Pacific Biosciences (Menlo Park, Calif.). In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in and out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used in the methods of the provided invention is nanopore sequencing (Soni, G. V., and Meller, A., Clin Chem 53: 1996-2001 (2007)). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used in the methods of the provided invention involves using a chemical-sensitive field effect transistor (chemFET) array to sequence DNA (for example, as described in U.S. Pub. 2009/0026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used in the methods of the provided invention involves using an electron microscope (Moudrianakis E. N. and Beer M., PNAS, 53:564-71 (1965)). In one example of the technique, individual DNA molecules are labeled using metallic labels that are distinguishable using an electron microscope. These molecules are then stretched on a flat surface and imaged using an electron microscope to measure sequences.

Detection

Nucleic acid sequences obtained from the various bacteria can then be compared in any number of ways, including ribotyping, rep-PCR, optical mapping, and Pulsed field gel electrophoresis. Ribotyping involves the fingerprinting of genomic DNA restriction fragments that contain all or part of the geens for the 16S and 23S ribosomal RNA ("rRNA"). Accordingly, ribotyping can be used to identify and classify bacteria based on differences in rRNA. DNA is extracted from a colony of bacteria and then enzymatically restricted into discrete-sized fragments. The DNA is then transferred to a membrane and probed with a region of the rRNA operon to reveal the pattern of rRNA genes. The pattern is recorded, digitized, and stored in a database. The variations that exist among the pathogens in both the position and intensity of rRNA bands can be used for their classification and identification. In other aspects, gel electrophoresis is conducted with the digested samples, whereupon the fragments are visualized as lines on the gel. These lines form a unique pattern for each species and can be used to identify the origin of the DNA. Databases for *Listeria* (80 pattern types), *Salmonella* (97 pattern types), *Escherichia* (65 pattern types), and *Staphylococcus* (252 pattern types) have been established. Methods of ribotyping are well-known in the art. In a basic protocol, DNA is isolated from bacterial cell cultures and digested in separate reactions with two different restriction endonucleases. Digested fragments are then separated by mass and charge with gel electrophoresis. The DNA fragments are then transferred from the gel to a Nitran filter and probed with labeled rRNA from the particular species. The bound probes are then visualized according to the label used. Each ribotype (i.e., ribosome-associated fingerprint) is analyzed by assigning an alphanumeric pattern based on the distance between bands. Each unique banding pattern is deemed a ribotype and assigned an alphanumeric pattern. Further detail on such methods can be found, for example, in US 2005/0260293, incorporated by reference herein in its entirety.

Repetitive sequence-based PCR or rep-PCR provides another means for comparing pathogen genomes. Prokaryotic and eukaryotic genomes contain dispersed repetitive sequences separating longer single-copy DNA sequences. Interspersed repetitive sequences are characterized as relatively short (usually <500 bp), non-coding dispersed elements in bacterial genomes. Current data indicates that repetitive DNA comprises a substantial portion of the microbial genomes. Rep-PCR primers complement these repetitive sequences and allow for specific binding, providing reproducible, unique rep-PCR DNA fingerprint patterns.

In a basic protocol, nucleic acid is isolated from microorganisms of interest and allowed to hybridize to rep-PCR binders that bind to the many repetitive sequences interspersed throughout the genome. Multiple fragments of various lengths are then amplified. After amplification, the fragments are separated by electrophoresis according to their mass and charge. Based on the distribution and intensity of the bands, a unique rep-PCR DNA fingerprint profile is created. Additional detail on rep-PCR methods are provided in U.S. Pat. Nos. 5,691,136 and 5,523,217, herein incorporated by reference in its entirety.

Optical mapping is a method of whole genome analysis that involves the generation of ordered restriction maps for entire genomes called "optical maps." By mapping the location of restriction enzyme sites along the unknown DNA of an organism, the spectrum of resulting DNA fragments together serve as a unique fingerprint for that sequence. In a basic protocol, genomic DNA is obtained from lysed cells, and randomly fragmented to a produce a library of large genomic molecules for optical mapping. A single DNA molecule is then placed onto a slide under a fluorescent microscope. Restriction enzymes are added to digest the DNA at specific positions. Each DNA molecule is then stained with a fluorescent dye. DNA fragments stained with the dye are visualized by fluorescence microscopy and are sized by measuring the integrated fluorescent intensity. This results in an optical map of the single molecules. The individual optical maps are combined to produce a consensus, genomic, optical map. Microfluidic devices can be used in conjunction with optical mapping to improve efficiency and algorithms can be incorporated to determine the best consensus map. Further detail on optical mapping can be found in U.S. patent application Ser. Nos. 13/147,056 and 12/257,892, incorporated by reference herein in its entirety.

Pulse field gel electrophoresis (PFGE) has also been used to characterize various pathogens, such as bacteria. PFGE is a form of restriction fragment length polymorphism (RFLP) typing in which the bacterial genome is digested with rare cutting enzymes. These restriction enzymes cut genomic DNA infrequently and therefore generate a smaller number of DNA fragments 910-20 bands). These fragments, which can span a wide range of sizes, are separated using specialized electrophoresis techniques. Differences in the restriction profiles are used to conduct genetic comparisons among isolates. Analysis can be performed by computer, enabling rapid and easy comparison between strains. PFGE electrophoresis techniques are well-known in the art. Further detail on such methods is provided, for example, in U.S. Pat. No. 7,731,828 and U.S. patent application Ser. No. 10/418,837, herein incorporated by reference in its entirety.

Microarray-based measurements of single-nucleotide polymorphisms can also be used. An array is an orderly arrangement of samples where matching of known and unknown DNA samples is performed using base paring rules. An array experiment makes use of common assay systems such as microplates or standard blotting membranes. The sample spot sizes are typically less than 200 microns in diameter. Thousands of spotted samples known as probes are immobilized onto a solid support. The probes can include DNA, cDNA, or oligonucleotides. These are used to determine the complementary binding of the unknown sequences, therefore allowing parallel analysis for gene expression and discovery. In certain aspects, genomic DNA is used. The genes might differ from each other by as little as a single nucleotide base. This single base difference between two sequences is known as a single nucleotide polymorphism (SNP). SNPs can be used to distinguish between otherwise highly similar strains of bacteria. The use of microarrays to detect and differentiate microorganisms such as bacteria is well-known in the art. Additional detail can be found, for example, in Zhou et al., Microarrays for bacterial detection and microbial community analysis, Current Opinion in Microbiology, 2003, 6: 288-294, and U.S. patent application Ser. No. 10/418,837, each of which are incorporated by reference in its entirety.

Classification

In an aspect of the invention, species that are genetically-similar or closely related are identified and grouped so that a representative species may be used to represent the entire grouping in antibody production. The groupings serve as guides to selection of a minimal subset of strains representative of the spectrum of genomic variation existing within each species. With sequencing, the entire genome of a species (such as bacteria) can be obtained and analyzed for genetic relationships and similarities. For bacteria, pathogens, viruses, etc., the entire genome or specific genes within the genome can be compared for distinguishing species or classes. See for example Syst Appl Microbiol. 2010 June; 33(4):175-82. doi: 10.1016/j.syapm.2010.03.003. Epub 2010 Apr. 20, which is incorporated by reference and discusses revealing phylogenetic coherence by 16S rRNA gene analyses.

It would be appreciated that the percentage of similarities to which to base a determination of grouping can vary depending on the species. For example, a method could be employed that groups pathogens together based upon a 97% similarity determination. Other methods could employ grouping based upon a 92% similarity determination. Other methods could employ grouping based upon a 85% grouping determination.

Historically, bacteria and other microorganisms were classified based upon shape and staining methods. However, advances in sequencing provide for the opportunity to reconcile microbial systematics and genomics. See Syst Appl Microbiol. 2010 June; 33(4):175-82. doi, 10.1016/j.syapm.2010.03.003. Epub 2010 Apr. 20. Classifying or grouping pathogens or bacteria on the basis of genomic similarities allows for prediction of common antigens or surface proteins.

The present invention provides a method that incorporates using DNA sequencing data to determine genetic relatedness for the purposes of grouping, not based on shape or staining methods, but on genomic similarities. Classification and analysis based upon genomes or DNA sequencing allows for genetically similar bacteria to be determined. Whole-genome sequences can also be quantified to measure divergence due to all processes, including vertical and horizontal transfer and genome reduction. See IJSEM November 2003 vol. 53 no. 6 1893-1900, which is incorporated by reference.

Once the sequences are compared using any of the above methods, similar sequences may be matched together using classification schemes known in the art, including the preparation of cladograms. A cladogram is a branching, tree-like diagram in which the endpoints of the branches represent specific species of organisms. It is used to illustrate phylogenetic relationships and show points at which various species have diverged from common ancestral forms. Although cladograms have traditionally been constructed largely on the basis of morphological characteristics, DNA and RNA sequencing data can also be used to prepare cladograms. Cladograms are constructed by grouping organisms together based on their shared derived characteristics.

A greatly simplified procedure for generating a cladogram involves the steps of gathering and organizing data, considering the possible cladograms, and from those cladograms, selecting the best cladogram. Cladistic analysis begins by compiling the list of taxa to be organized; the list of characteristics to be compared; and for each taxon, the values of each of the listed characteristics. For example, if analyzing 20 different strains of bacterial within a species, the data might comprise the list of the 20 strains; the list of characteristics might comprise only genome sequence information; and for each of the 20 strains, its particular genome sequence. All the data are then organized into a taxon-character matrix, which is then used to perform the phylogenetic analysis.

The inference of phylogenies from genetic data can incorporate various statistical methods, such as use of a parsimony criterion, maximum likelihood models, Bayesian inference, and the use of genomic retrotransposon markers.

The consideration of potential cladograms is typically performed by computer. A typical cladistics program begins by using heuristic techniques to identify a small number of candidate cladograms. Many cladistics programs then continue the search by repeating the following steps: evaluation of the candidate cladograms by comparing them to the characteristic data; identification of the best candidates that are most consistent with the characteristic data; creation of additional candidates by creating several variants of each of the candidates from the prior step; use of heuretics to create several new candidate cladograms unrelated to the prior candidates; repeating these steps until no further improvement is observed.

In selecting the best cladogram, an algorithm may be used. The algorithm may be implemented by computer. Most algorithms use a metric to determine how consistent a candidate cladogram is with the data. Most cladogram algorithms use the mathematical techniques of optimization and minimization. Algorithms for cladograms can further include least squares, neighbor-joining, parsimony, maximum likelihood, and Bayesian inference. Further detail on the generation of cladograms is provided in U.S. Pat. No. 7,043,371, incorporated by reference herein in its entirety. Once the cladograms have been prepared, the cladogram can be used to identify minimally different subsets of bacteria. These minimally different subsets can then be used to generate target specific binding moieties. Using DNA sequencing whole genome sequences can be employed to determine genetic closeness among related bacteria. See for example, Nature. 2009 Dec. 24; 462(7276): 1056-1060, doi: 10.1038/nature08656, which discusses sequencing and analyzing genomes of Bacteria and Archaea for reconstruction of phylogenetic history and the discovery of new protein families and biological properties for prediction functions of known genes. Genetic similarities can be indicative of surface protein or antigenic similarities and provide a method for grouping pathogens by their genomes.

Once the genomic sequence is identified, as discussed above, the critical genetic characteristics of major antigens of the pathogen can be identified, which can be implemented in organizing groups into subgroups in order to find representative species. See for example Korean J Parasitol. 2009 October; 47(Suppl): S51-S58, Published online 2009 Oct. 26. doi: 10.3347/kjp.2009.47.S.S51, wherein the Plasmodium vivax protozoan pathogen genomic sequence is analyzed for identification of major antigens of the pathogen. Therefore, instead of selecting a group based upon whole genomic similarity, groups could also be formed by the genetic similarities within surface protein or antigen genes. The genomic make-up of the groups of pathogens can be employed to identify genes related to surface proteins or antigens common within a group. The surface proteins or antigens associated or common within a group of the pathogens, can be determined by known methods in the art. See for example Genes & Genetic Systems [2004, 79(3):129-137], DOI: 10.1266/ggs.79.129, which discloses the identification of surface protein antigen genes. Surface proteins are likely to interact with the host immune system and are ideal candidates for vaccine development. In this aspect of the invention, identifying or grouping species based upon associated antigen genes allows for selection of a representative species or species. In an example, a series of monoclonal antibodies were isolated which reacted with one of two major surface proteins of rhesus rotavirus, and effectively neutralized the rhesus rotavirus. See J. Virol. August 1983 vol. 47 no. 2 267-275, which is incorporated by reference.

Antibody Production

General methodologies for antibody production, including criteria to be considered when choosing an animal for the production of antisera, are described in Harlow et al. (Antibodies, Cold Spring Harbor Laboratory, pp. 93-117, 1988). For example, an animal of suitable size such as goats, dogs, sheep, mice, or camels are immunized by administration of an amount of immunogen, such as the target bacteria, effective to produce an immune response. An exemplary protocol is as follows. The animal is injected with 100 milligrams of antigen resuspended in adjuvant, for example Freund's complete adjuvant, dependent on the size of the animal, followed three weeks later with a subcutaneous injection of 100 micrograms to 100 milligrams of immunogen with adjuvant dependent on the size of the animal, for example Freund's incomplete adjuvant. Additional subcutaneous or intraperitoneal injections every two weeks with adjuvant, for example Freund's incomplete adjuvant, are administered until a suitable titer of antibody in the animal's blood is achieved. Exemplary titers include a titer of at least about 1:5000 or a titer of 1:100,000 or more, i.e., the dilution having a detectable activity. The antibodies are purified, for example, by affinity purification on columns containing protein G resin or target-specific affinity resin.

The technique of in vitro immunization of human lymphocytes is used to generate monoclonal antibodies. Techniques for in vitro immunization of human lymphocytes are well known to those skilled in the art. See, e.g., Inai, et al., Histochemistry, 99(5):335 362, May 1993; Mulder, et al., Hum. Immunol., 36(3):186 192, 1993; Harada, et al., J. Oral Pathol. Med., 22(4):145 152, 1993; Stauber, et al., J. Immunol. Methods, 161(2):157 168, 1993; and Venkateswaran, et al., Hybridoma, 11(6) 729 739, 1992. These techniques can be used to produce antigen-reactive monoclonal antibodies, including antigen-specific IgG, and IgM monoclonal antibodies.

Compositions of the invention may be designed to isolate different species of bacteria. These different species may include gram positive bacteria, gram negative bacteria, or a combination of gram positive and gram negative bacteria. Such compositions allow for isolation of essentially all bacteria from a sample.

In still other embodiments, compositions are designed to isolate specific pathogen from a sample. Exemplary bacterial species that may be captured and isolated by methods of the invention include *E. coli, Listeria, Clostridium, Mycobacterium, Shigella, Borrelia, Campylobacter, Bacillus, Salmonella, Staphylococcus, Enterococcus, Pneumococcus, Streptococcus*, and a combination thereof. These sets can be mixed together to isolate for example, *E. coli* and *Listeria*; or *E. coli, Listeria*, and *Clostridium*; or *Mycobacterium, Campylobacter, Bacillus, Salmonella*, and *Staphylococcus*, etc. Any combination of sets may be used and compositions of the invention will vary depending on the suspected pathogen or pathogens to be isolated.

A suitable nucleic acid probe assay generally includes sample treatment and lysis, hybridization with selected probe(s), hybrid capture, and detection. Lysis of the bacteria is necessary to release the nucleic acid for the probes. The nucleic acid target molecules are released by treatment with any of a number of lysis agents, including alkali (such as NaOH), guanidine salts (such as guanidine thiocyanate), enzymes (such as lysozyme, mutanolysin and proteinase K), and detergents. Lysis of the bacteria, therefore, releases both DNA and RNA, particularly ribosomal RNA and chromosomal DNA both of which can be utilized as the target molecules with appropriate selection of a suitable probe. Use of rRNA as the target molecule(s), may be advantageous because rRNAs constitute a significant component of cellular mass, thereby providing an abundance of target molecules. The use of rRNA probes also enhances specificity for the bacteria of interest, that is, positive detection without undesirable cross-reactivity which can lead to false positives or false detection.

Hybridization includes addition of the specific nucleic acid probes. In general, hybridization is the procedure by which two partially or completely complementary nucleic acids are combined, under defined reaction conditions, in an anti-parallel fashion to form specific and stable hydrogen bonds. The selection or stringency of the hybridization/ reaction conditions is defined by the length and base composition of the probe/target duplex, as well as by the level and geometry of mis-pairing between the two nucleic acid strands. Stringency is also governed by such reaction parameters as temperature, types and concentrations of denaturing agents present and the type and concentration of ionic species present in the hybridization solution.

The hybridization phase of the nucleic acid probe assay is performed with a single selected probe or with a combination of two, three or more probes. Probes are selected having sequences which are homologous to unique nucleic acid sequences of the target organism. In general, a first capture probe is utilized to capture formed hybrid molecules. The hybrid molecule is then detected by use of antibody reaction or by use of a second detector probe which may be labelled with a radioisotope (such as phosphorus-32) or a fluorescent label (such as fluorescein) or chemiluminescent label.

Detection of bacteria of interest can also be performed by use of PCR techniques. A suitable PCR technique is described, for example, in Verhoef et al. (WO 92/08805). Such protocols may be applied directly to the bacteria captured on the magnetic particles. The bacteria are combined with a lysis buffer and collected nucleic acid target molecules are then utilized as the template for the PCR reaction.

For detection of the selected bacteria by use of antibodies, isolated bacteria are contacted with antibodies specific to the bacteria of interest. As noted above, either polyclonal or monoclonal antibodies can be utilized, but in either case have affinity for the particular bacteria to be detected. These antibodies will adhere/bind to material from the specific target bacteria. With respect to labeling of the antibodies, these are labeled either directly or indirectly with labels used in other known immunoassays. Direct labels may include fluorescent, chemiluminescent, bioluminescent, radioactive, metallic, biotin or enzymatic molecules. Methods of combining these labels to antibodies or other macromolecules are well known to those in the art. Examples include the methods of Hijmans, W. et al. (1969), Clin. Exp. Immunol. 4, 457-, for fluorescein isothiocyanate, the method of Goding, J. W. (1976), J. Immunol. Meth. 13, 215-, for tetramethylrhodamine isothiocyanate, and the method of Ingrall, E. (1980), Meth. in Enzymol. 70, 419-439 for enzymes.

These detector antibodies may also be labeled indirectly. In this case the actual detection molecule is attached to a secondary antibody or other molecule with binding affinity for the anti-bacteria cell surface antibody. If a secondary antibody is used it is preferably a general antibody to a class of antibody (IgG and IgM) from the animal species used to raise the anti-bacteria cell surface antibodies. For example, the second antibody may be conjugated to an enzyme, either alkaline phosphatase or to peroxidase. To detect the label, after the bacteria of interest is contacted with the second antibody and washed, the isolated component of the sample is immersed in a solution containing a chromogenic substrate for either alkaline phosphatase or peroxidase. A chromogenic substrate is a compound that can be cleaved by an enzyme to result in the production of some type of detectable signal which only appears when the substrate is cleaved from the base molecule. The chromogenic substrate is colorless, until it reacts with the enzyme, at which time an intensely colored product is made. Thus, material from the bacteria colonies adhered to the membrane sheet will become an intense blue/purple/black color, or brown/red while material from other colonies will remain colorless. Examples of detection molecules include fluorescent substances, such as 4-methylumbelliferyl phosphate, and chromogenic substances, such as 4-nitrophenylphosphate, 3,3', 5,5'-tetramethylbenzidine and 2,2'-azino-di-[3-ethelbenzthiazoliane sulfonate (6)]. In addition to alkaline phosphatase and peroxidase, other useful enzymes include β-galactosidase, β-glucuronidase, α-glucosidase, β-glucosidase, α-mannosidase, galactose oxidase, glucose oxidase and hexokinase.

A preferred embodiment would entail employing genotyping to survey the extent of genetic variation within a species. Once genomes have been identified, the genomes are grouped so that each group member is 97% similar to other group members. Within the grouped genomically-similar isolates, one isolate from each group is selected to represent the entire group. Cadograms could be employed to guide selection of a minimal subset of strains representative of the spectrum of genomic variation within each species. Each representative is then used in antibody production as immunogens to produce a spectrum of antibodies to address pathogens within a species.

Incorporation by Reference

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method of generating antibodies against a species comprising pathogens, the method comprising:
    obtaining a nucleic acid from a plurality of pathogens within the species;
    assaying said nucleic acids to determine genetic similarities between the pathogens, wherein assaying comprises assessing the level of similarity by an analytical method selected from the group consisting of ribotyping, rep-PCR, pulsed field gel electrophoresis, optical mapping, and microarray-based measurement of single nucleotide polymorphisms;
    separating the pathogens into at least two different groups based upon the genetic similarities;
    isolating at least one, but not all, pathogen from each group that exhibits representative characteristics of the group to form a subset of pathogens; and
    generating antibodies for each isolated pathogen by administering each isolated pathogen to one or more mammals in an amount effective to produce an immune response in order to produce a set of antibodies.

2. The method of claim 1, wherein the nucleic acid is DNA.

3. The method of claim 1, wherein the pathogen comprises bacteria.

4. The method of claim 3, wherein the bacteria comprise bacteria of the same species but of different serotypes.

5. The method of claim 3, wherein the bacteria comprise bacteria of the same species but of different strains.

6. The method of claim 1, wherein assaying said nucleic acids comprises sequencing a portion of said nucleic acids and comparing the sequences.

7. The method of claim 1, wherein administering comprises injecting a mammal with each isolated pathogen.

8. The method of claim 7, wherein generating an antibody further comprises placing the pathogen in adjuvant prior to injecting the mammal.

9. The method of claim 1, wherein the antibodies are monoclonal antibodies.

10. The method of claim 1, wherein the antibodies are polyclonal antibodies.

11. The method of claim 1, wherein isolating the at least one pathogen comprises building a cladogram where genomically similar pathogens are grouped together to form clades.

12. The method of claim 1, wherein the subset of pathogens is representative of the genomic variation present in the species of pathogen.

13. The method of claim 1, wherein the nucleic acid is RNA.

* * * * *